US009623171B2

(12) United States Patent
Okihara et al.

(10) Patent No.: US 9,623,171 B2
(45) Date of Patent: Apr. 18, 2017

(54) MEDICAL DEVICE PACKAGE

(71) Applicant: Terumo Kabushiki Kaisha, Tokyo (JP)

(72) Inventors: Hitoshi Okihara, Fujinomiya (JP); Shingo Koyama, Fujinomiya (JP); Koji Nakamura, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/464,195

(22) Filed: Aug. 20, 2014

(65) Prior Publication Data

US 2014/0353190 A1    Dec. 4, 2014

Related U.S. Application Data

(63) Continuation of application No. PCT/JP2013/053539, filed on Feb. 14, 2013.

(30) Foreign Application Priority Data

Feb. 20, 2012  (JP) .................................. 2012-033556

(51) Int. Cl.
| | |
|---|---|
| *B65D 83/00* | (2006.01) |
| *A61M 5/00* | (2006.01) |
| *A61M 5/32* | (2006.01) |

(52) U.S. Cl.
CPC .......... *A61M 5/002* (2013.01); *A61M 5/3202* (2013.01); *A61M 5/001* (2013.01)

(58) Field of Classification Search
CPC ......... B65B 55/00; B65B 55/02; B65B 55/04; B65B 55/06; B65B 55/08; B65B 55/10;
(Continued)

(56) References Cited

U.S. PATENT DOCUMENTS 4,444,310 A    4/1984  Odell
4,606,083 A *  8/1986  Kingston ............... A47K 3/001
                                                    220/215
(Continued)

FOREIGN PATENT DOCUMENTS

BE          1018901 A4       10/2011
DE    1020080 46 378 A1      3/2011
(Continued)

OTHER PUBLICATIONS

International Search Report dated Apr. 16, 2013 issued in Application No. PCT/JP2013/053539.
(Continued)

*Primary Examiner* — Steven A. Reynolds
*Assistant Examiner* — Javier A Pagan
(74) *Attorney, Agent, or Firm* — Foley & Lardner LLP

(57) ABSTRACT

A medical device package includes a medical device including a first end surface and a second end surface; and a medical device storage container configured to store the medical device, the medical device storage container including a container main body and a holding unit located in the storage space, and configured to hold the medical device such that the first end surface faces upward; and a sheet-like sealing member adapted to be glued to the container main body to seal an opening of the container main body. A surface of the sealing member that faces the container main body includes an adhesive applied area on which an adhesive is applied and an adhesive non-applied area on which the adhesive is not applied, the adhesive non-applied area being an area facing at least the first end surface of the medical device held by the holding unit.

12 Claims, 7 Drawing Sheets

(58) Field of Classification Search
CPC ......... B65B 55/12; B65B 55/14; B65B 55/16; B65B 55/18; A61M 5/00; A61M 5/001; A61M 5/002; A61M 5/008
USPC ....... 206/363, 364, 365, 366, 367, 368, 369, 206/370, 439
See application file for complete search history.

(56) References Cited

U.S. PATENT DOCUMENTS

| | | | |
|---|---|---|---|
| 6,189,292 | B1* | 2/2001 | Odell et al. .................... 53/425 |
| 7,296,678 | B2 | 11/2007 | Raynal-Olive et al. |
| 7,431,157 | B2* | 10/2008 | Porret et al. .................. 206/439 |
| 8,028,835 | B2* | 10/2011 | Yasuda et al. ............. 206/459.1 |
| 2004/0096909 | A1 | 5/2004 | Kamei et al. |
| 2008/0173563 | A1 | 7/2008 | Perot |
| 2012/0204516 | A1* | 8/2012 | Palumbo ............... B65B 31/028 53/403 |
| 2013/0161225 | A1 | 6/2013 | Lepot |

FOREIGN PATENT DOCUMENTS

| | | |
|---|---|---|
| FR | 2911072 A1 | 7/2008 |
| JP | 2002-053169 A | 2/2002 |
| JP | 2002-505980 A | 2/2002 |
| JP | 2004-513707 A | 5/2004 |
| JP | 2009-183768 A | 8/2009 |
| WO | WO-99/45984 A1 | 9/1999 |
| WO | WO-02/40063 A1 | 5/2002 |
| WO | WO-02/40064 A1 | 5/2002 |
| WO | WO-03/094999 A1 | 11/2003 |

OTHER PUBLICATIONS

Extended European Search Report dated Jun. 29, 2015 issued in Application No. 13751707.4.

\* cited by examiner

FIG. 9
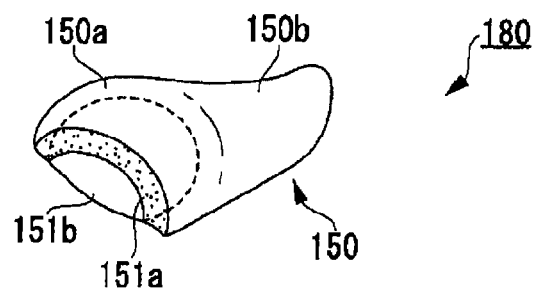
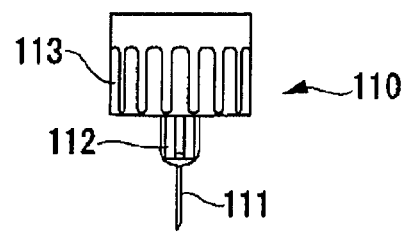
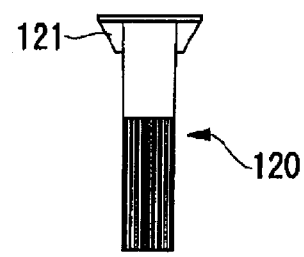
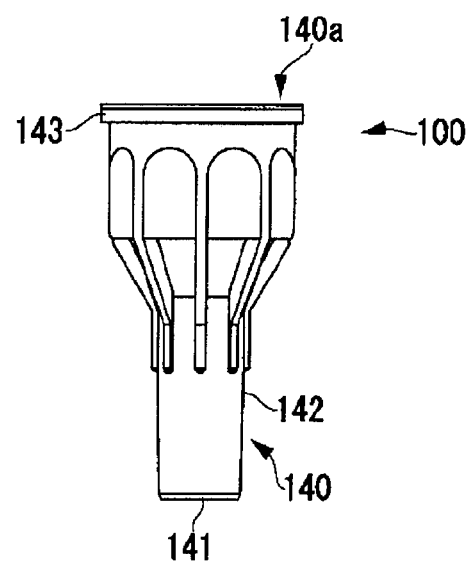

MEDICAL DEVICE PACKAGE

CROSS-REFERENCE TO RELATED APPLICATION

This application is a continuation application filed under 35 U.S.C. 111(a) claiming the benefit under 35 U.S.C. §§120 and 365(c) of PCT International Application No. PCT/JP2013/053539, filed on Feb. 14, 2013, which is based upon and claims the benefit of priority of Japanese Application No. 2012-033556, filed on Feb. 20, 2012, the entire contents of which are hereby incorporated by reference in their entireties.

BACKGROUND

Technical Field

The present disclosure relates to a medical device package that stores medical devices, such as syringes and connectors.

Background Art

Conventionally, for conveyance or storage of syringes before being filled with a drug solution or the like, syringe storage containers capable of holding and storing a plurality of syringes in an upright state are widely used. Such syringe storage containers are provided with a box-shaped container main body having an upper surface opening, a holder that holds the plurality of syringes in an upright state, and a sealing member that seals the opening of the container main body.

A shelf-like portion that supports the holder is provided inside the container main body. The holder is formed into a plate shape having a plurality of through-holes. The syringe is inserted into the through-hole of the holder, and a flange portion provided at an end portion of the syringe is hooked on a peripheral edge of the through-hole, so that the syringe is held in the holder. When such a syringe storage container is used, a plurality of syringes can be held in an upright state such that filling openings for the drug solution face upward.

Typically, manufacturing of the syringes is performed in a place different from a place where the drug solution is filled. At the place where the syringes are manufactured, manufactured syringes are stored in the syringe storage container, the opening of the syringe storage container is sealed with the sealing member, and the medical device package is assembled. Following that, sterilization processing is applied to the syringe storage container by causing a high-temperature vapor or gas to permeate the sealing member, such as high-pressure vapor sterilization (autoclave) or ethylene oxide gas (EOG) sterilization.

The syringe storage container to which the sterilization processing has been applied is conveyed to the place where the drug solution is filled. At the place where the drug solution is filled, the sealing of the syringe storage container with the sealing member is released, and the holder in which the plurality of syringes is held is taken out from the container main body, and is set to a filling device for filling the drug solution. Following that, the drug solution is filled in the syringes.

A container that stores medical devices is described in JP 2009-183768 Av, for example. The medical container described in JP 2009-183768 A includes a tray that supports a syringe body, a vessel into which the tray is fit in, a protection sheet that covers the tray and the syringe body, and a cover sheet that seals the vessel. The cover sheet is a gas permeable material such as nonwoven polyolefin, and is glued to a flange of the vessel in a peelable manner. An adhesive to be applied on the cover sheet is applied on one surface at a side facing the flange of the vessel. The protection sheet is arranged inside the vessel, and is used to prevent bacteria, dust, and the like from entering the syringes after the cover sheet is peeled from the vessel.

However, in the medical container described in Patent Literature 1, when the sterilization processing is applied to the vessel using a high-temperature vapor or gas, the cover sheet is pressed by the vapor or the gas and is deformed to be dented into the vessel. Therefore, the surface of the cover sheet, on which the adhesive is applied, comes in contact with the protection sheet, and the protection sheet is glued by the cover sheet.

If the protection sheet is glued by the cover sheet, the protection sheet is removed together with the cover sheet when the cover sheet is peeled from the vessel. Therefore, when the cover sheet is peeled from the vessel, the syringe is exposed, and bacteria, dust, and the like may enter the syringe.

When the cover sheet is peeled from the vessel in an environment where there are no bacteria, dust, and the like, the protection sheet may not be used. However, in this case, when the sterilization processing is applied to the vessel using a high-temperature vapor or gas, the surface of the cover sheet, on which the adhesive is applied, comes in contact with the syringe. As a result, the syringe may be glued by the cover sheet, or the adhesive may be transferred to the syringe and attached as a foreign substance. This is not favorable.

SUMMARY OF THE INVENTION

Embodiments of the present invention has been made in view of the foregoing, and one objective is to provide a medical device package in which an adhesive on a cover sheet (sealing member) is not attached to a protection sheet or a medical device in a vessel even if sterilization processing is applied to the vessel (container main body) using a vapor or a gas.

To solve certain problems with the prior art devices and to achieve certain objectives of embodiments of the present invention, the medical device package of one embodiment of present invention includes a medical device including a first end surface and a second end surface, and a medical device storage container that stores the medical device. The medical device storage container includes a container main body and a sheet-like sealing member.

The container main body includes a peripheral wall portion including an upper end portion and a lower end portion, a bottom continuing to the lower end portion and surrounded by the lower end portion, an opening surrounded by the upper end portion, a storage space formed of the peripheral wall portion, the bottom, and the opening, and a holding unit provided in the storage space and which holds the medical device such that the one end surface faces upward.

The sealing member is glued to the container main body, and seals the opening of the container main body. A surface of the sealing member, which faces the container main body, includes an adhesive applied area on which an adhesive is applied and an adhesive non-applied area on which the adhesive is not applied. Then, the adhesive non-applied area is an area facing at least the first end surface of the medical device held in the holding unit.

In the medical device package of the present invention, the adhesive non-applied area of the sealing member is set to an area facing at least the first end surface of the medical device held in the holding unit. Therefore, even if the sealing member comes in contact with the first end surface of the medical device held in the holding unit when the sealing member is pressed by a vapor or a gas, and is deformed to be dented into the container main body at the time of the sterilization processing, the adhesive is not attached to the medical device. As a result, the medical device is not glued by the sealing member, and the medical device can be kept in a favorable state.

Further, when an inner sheet (protection sheet) is arranged between the medical device and the sealing member, the adhesive is not attached to the inner sheet even if the sealing member comes in contact with the inner sheet.

In one embodiment, a medical device package includes a medical device including a first end surface and a second end surface; and a medical device storage container adapted to store the medical device. The medical device storage container includes a container main body including a peripheral wall portion including an upper end portion and a lower end portion, a bottom continuing to the lower end portion, and surrounded by the lower end portion, an opening surrounded by the upper end portion, a storage space formed of the peripheral wall portion, the bottom, and the opening, and a holding unit provided in the storage space, and adapted to hold the medical device such that the first end surface faces upward, and a sheet-like sealing member adapted to be glued to the container main body to seal the opening of the container main body, and a surface of the sealing member, the surface facing the container main body, includes an adhesive applied area on which an adhesive is applied and an adhesive non-applied area on which the adhesive is not applied, and the adhesive non-applied area is an area facing at least the first end surface of the medical device held in the holding unit.

In one aspect, the medical device is a syringe including the first end surface and the second end surface, and provided with a filling opening for allowing a drug solution to be filled in the one end surface. The holding unit is made of a syringe holding member engaged with an inner surface of the peripheral wall portion to face the bottom, and adapted to hold the syringe such that the first end surface of the syringe faces upward.

In one aspect, the medical device package includes an inner sheet adapted to cover a side of the first end surface of the syringe held in the syringe holding member.

In one aspect, the adhesive non-applied area is an area facing at least the inner sheet.

In one aspect, the adhesive non-applied area is an area facing at least the opening.

In one aspect, the syringe includes a discharge portion forming the second end surface and adapted to discharge the drug solution.

In one aspect, the container main body includes a flange portion continuing to the upper end portion, and surrounding the upper end portion, and the sealing member is glued to the flange portion.

In one aspect, the sealing member is glued to the container main body by a heat meltable adhesive.

In one aspect, the medical device stored in the container main body is sterilizable using a high-pressure vapor that permeates the sealing member.

According to the medical device package of embodiments of the present invention, even if sterilization processing is applied to the container main body using a vapor or a gas, an adhesive can be made not to attach a medical device in a container main body.

BRIEF DESCRIPTION OF THE DRAWINGS

FIG. 9 is an exploded view of the medical device package according to the fourth embodiment of the present invention.

DETAILED DESCRIPTION

Figure 1:
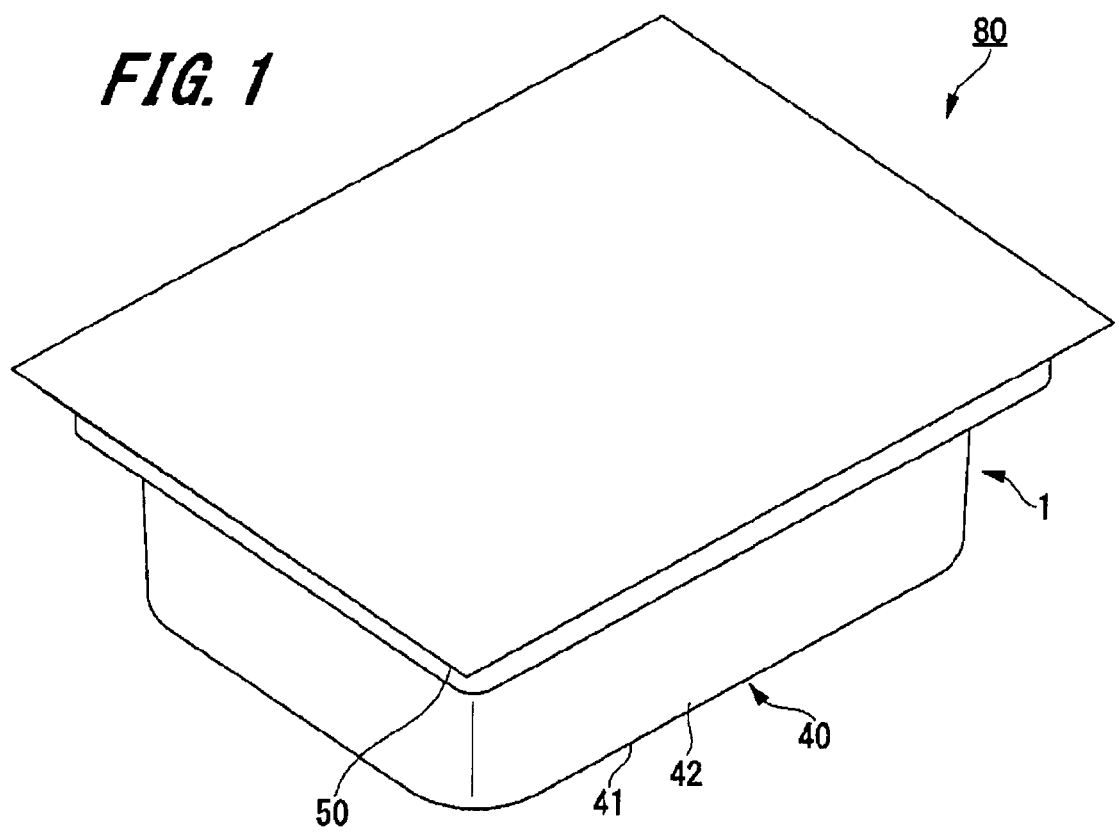
FIG. 1 is a perspective view of a medical device package according to a first embodiment of the present invention.

Hereinafter, embodiments of a medical device package according to embodiments of the present invention will be described with reference to FIGS. 1 to 9. Note that a common member in the drawings is denoted with the same reference sign. Further, the present invention is not limited to the embodiments below.

The description will be given in the following order.
1. First Embodiment of Medical Device Package
2. Second Embodiment of Medical Device Package
3. Third Embodiment of Medical Device Package
4. Fourth Embodiment of Medical Device Package
5. Modification 1. First Embodiment of Medical Device Package

[Configuration of Medical Device Package]

First, a configuration of a medical device package according to the first embodiment will be described with reference to FIGS. 1 and 2.

FIG. 1 is a perspective view of a medical device package according to the first embodiment of the present invention. FIG. 2 is an exploded perspective view of the medical device package according to the first embodiment of the present invention.

Figure 2:
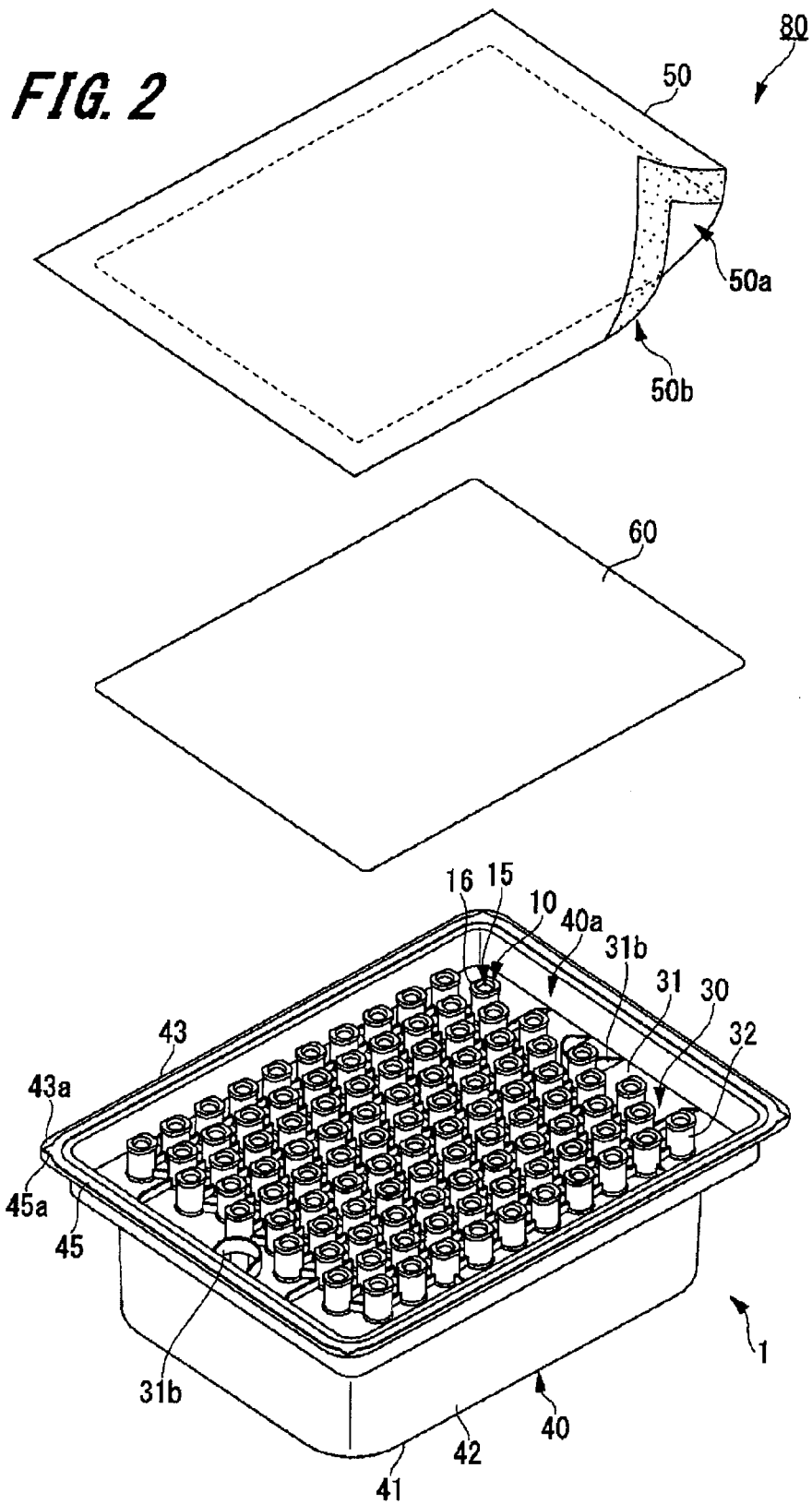
FIG. 2 is an exploded perspective view of the medical device package according to the first embodiment of the present invention.

As illustrated in FIGS. 1 and 2, a syringe package 80 representing a medical device package according to the first embodiment is configured from a syringe storage container 1 representing a specific example of a medical device storage container, and a syringe 10 (see FIG. 2) representing a specific example of a medical device stored in the syringe storage container 1.

The syringe storage container 1 is used to convey or store a plurality of syringes 10 at the same time. The syringe storage container 1 includes a syringe holding member 30 that holds the plurality of syringes 10, a container main body 40 that stores the syringe holding member 30 holding the plurality of syringes 10, a sealing member 50, and an inner sheet 60.

[Syringe Holding Member]

The syringe holding member 30 represents a specific example of a holding unit according to the present invention, and holds the syringes 10 in a state where filling openings 15 described below face upward. The syringe holding member 30 is placed on a mounting shelf 44 having a surface 44a (see FIG. 3) described below of the container main body 40, and faces a bottom 41 described below of the container main body 40.

The syringe holding member 30 includes a square flat base plate 31, and a cylinder portion 32 that protrudes from one surface of the base plate 31. The base plate 31 is provided with a plurality of through-holes 31a (see FIG. 5) for allowing the syringes 10 to be inserted.

The through-hole 31a is formed into a circular shape, and its diameter is larger than an outer diameter of a syringe main body 11 described below of the syringe 10. The plurality of through-holes 31a is arranged in the base plate 31 in a zigzag manner. Therefore, distances between adjacent through-holes 31a become equal, and thus contact of the adjacent syringes 10 during conveyance of the syringe storage container 1 can be suppressed.

As illustrated in FIG. 2, notches 31b are formed in two facing sides of the base plate 31, respectively. The user can easily take out the syringe holding member 30 locked in the container main body 40 by inserting his/her fingers into the notches 31b.

The cylinder portion 32 is formed to cover the through-hole 31a of the base plate 31, and includes a cylindrical hole 32a (see FIG. 5) for allowing the syringe 10 to be inserted. The cylindrical hole 32a communicates into the through-hole 31a. The diameter of the cylindrical hole 32a is approximately equal to the diameter of the through-hole 31a. A flange portion 16 described below of the syringe 10 is engaged with the cylinder portion 32.

[Inner Sheet]

The inner sheet 60 is formed into a square sheet shape. The area of the inner sheet 60 is set to have a size that covers a side of the filling openings 15 described below of the syringes 10 held in the syringe holding member 30. The inner sheet 60 is placed on the flange portions 16 described below of the syringes 10 held in the syringe holding member 30.

It is favorable that the inner sheet 60 is permeable by a gas for sterilization and is not permeable by minute particles such as bacteria or viruses. An example of a material for the inner sheet 60 includes Tyvek (registered trademark) that is a high-density polyethylene nonwoven fabric manufactured by Du Pont Kabushiki Kaisha. Note that the sealing member 50 formed of the high-density polyethylene nonwoven fabric is opaque.

[Container Main Body]

Next, the container main body 40 will be described with reference to FIG. 3.

Figure 3:
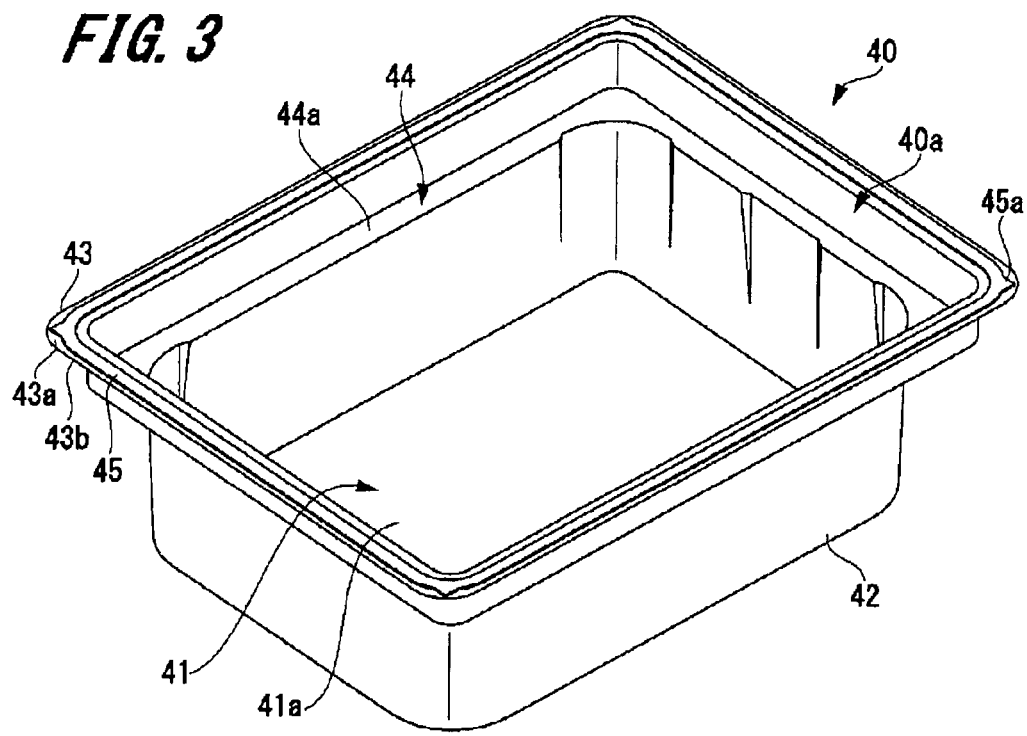
FIG. 3 is a perspective view of a container main body in the medical device package according to the first embodiment of the present invention.

FIG. 3 is a perspective view of the container main body 40.

As illustrated in FIG. 3, the container main body 40 includes a peripheral wall portion 42 including an upper end portion and a lower end portion, the bottom 41 continuing to the lower end portion of the peripheral wall portion 42 and surrounded by the lower end portion, an opening 40a surrounded by the upper end portion of the peripheral wall portion 42, and a flange 43 continuing to the upper end portion of the peripheral wall portion 42 and surrounding the upper end portion. An internal space of the container main body 40 surrounded by the peripheral wall portion 42, the bottom 41, and the opening 40a is a storage space that stores the syringe holding member 30 and the syringes 10.

The bottom 41 is formed into an approximately square plate shape, and configures a lower end of the container main body 40. The size of an inner surface 41a of the bottom 41 is formed smaller than the base plate 31 of the syringe holding member 30.

The flange 43 is approximately perpendicular to an upper end of the peripheral wall portion 42, and is formed into a square frame shape. The flange 43 includes an upper surface 43a facing an upper end and a lower surface 43b facing a lower end. The upper surface 43a and the lower surface 43b are formed into planes. An elongated protrusion 45 is formed on the upper surface 43a of the flange 43.

The elongated protrusion 45 is provided to surround the opening 40a, and is endlessly formed along the flange 43. That is, the elongated protrusion 45 is formed over the entire periphery of the flange 43. The sealing member 50 (see FIG. 2) is fused (glued) to the elongated protrusion 45. The width of the elongated protrusion 45 is set to be smaller than the width of the flange 43. The width of the elongated protrusion 45 is favorably 2 to 10 mm when considering to reliably fuse the sealing member 50 to seal the syringe storage container. Further, the height of the elongated protrusion 45 is favorably 0.2 to 0.5 mm or more.

An outline of an outer periphery of the elongated protrusion 45 is smaller than an outline of an outer periphery of the flange 43. Therefore, when the sealing member 50 is placed on the elongated protrusion 45, the sealing member 50 is less likely to bend toward the opening 40a of the container main body 40, and the sealing member 50 is reliably placed on the elongated protrusion 45. Therefore, the sealing member 50 can be reliably fused to the elongated protrusion 45. Further, when the sealing member 50 is peeled, an upper surface positioned at an outside of the elongated protrusion 45 on the flange 43 can be pressed, and thus the sealing member 50 can be easily peeled.

An outline of an inner periphery of the elongated protrusion 45 is larger than an outline of an outer periphery at the upper end of the peripheral wall portion 42. Therefore, when the sealing member 50 is heat-fused, a receiving jig (not illustrated) can support right under the elongated protrusion 45, and thus the sealing member 50 can be reliably fused to the elongated protrusion 45.

Further, the elongated protrusion 45 includes square shapes 45a. These square shapes 45a are arranged at four corners of the flange 43, and are formed to have right angles, respectively. Stress is concentrated on each of the square shapes 45a when the sealing member 50 is peeled from the container main body 40. As a result, the sealing member 50 can be easily peeled from the square shapes 45a. Further, since the square shapes 45a are positioned at the four corners of the flange 43, and thus when the sealing member 50 is peeled, the sealing member 50 can be always peeled from the specific places. Further, the sealing member 50 is not unintentionally peeled from places other than the four corners of the flange 43.

The container main body 40 and the syringe holding member 30 are favorably not denatured by sterilization processing using a high-temperature vapor or gas, such as high-pressure vapor sterilization (autoclave) or an ethylene oxide gas (EOG) sterilization. Examples of materials for the container main body 40 and the syringe holding member 30 include resins having excellent durability, such as polypropylene, polystyrene, polyethylene, polycarbonate, an ABS resin, and PET. Further, to secure visibility inside the container main body 40, the container main body 40 and the syringe holding member 30 are favorably substantially transparency or translucent, and examples of such materials include polycarbonate, polystyrene, and PET, of the above-described resins.

[Sealing Member]

Next, the sealing member 50 will be described with reference to FIG. 4.

Figure 4:
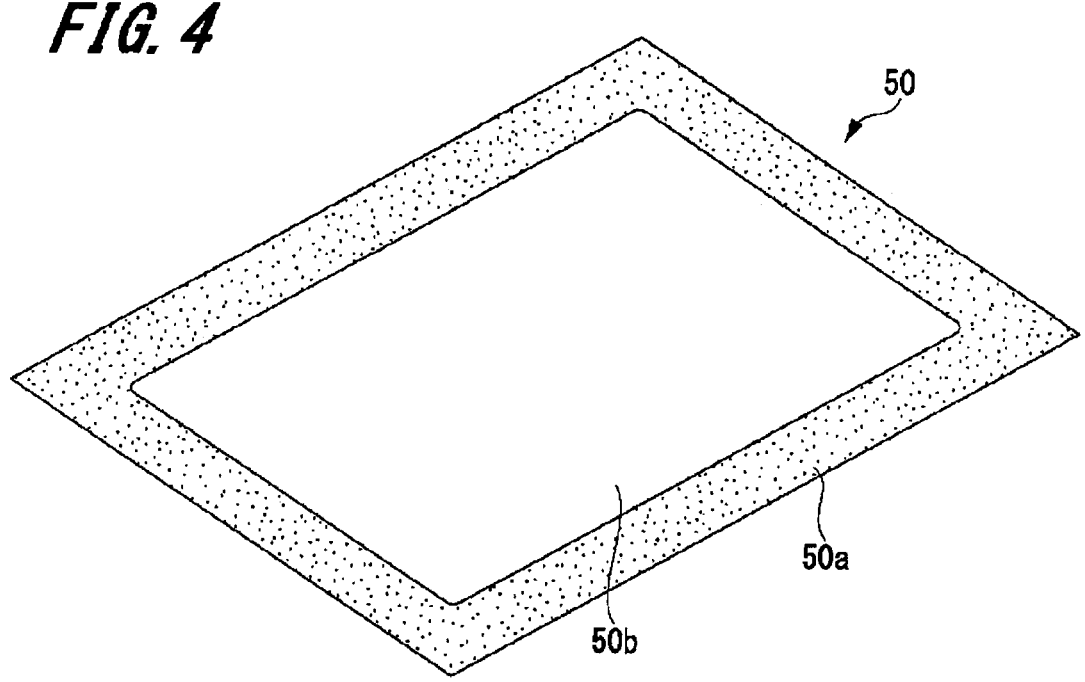
FIG. 4 is a perspective view of a sealing member in the medical device package according to the first embodiment of the present invention.

FIG. 4 is a perspective view of the sealing member 50 in a state where a surface of the sealing member 50, which faces the container main body 40, faces upward.

The sealing member 50 is formed into a square sheet shape approximately equal to the outline of the outer periphery of the flange 43 (see FIG. 3) of the container main body 40. That is, the outline of the outer periphery of the elongated protrusion 45 provided on the flange 43 is formed smaller than the outline of the outer periphery of the sealing member 50. The sealing member 50 is heat fused to the flange 43 of the container main body 40 using an adhesive. To be specific, the sealing member 50 is heat-fused to the elongated protrusion 45 on the flange 43.

It is favorable that the sealing member 50 is permeable by a gas for sterilization and is not permeable by minute particles such as bacteria or viruses. An example of a material for the sealing member 50 includes Tyvek (registered trademark) that is a high-density polyethylene nonwoven fabric manufactured by Du Pont Kabushiki Kaisha. Note that the sealing member 50 formed of the high-density polyethylene nonwoven fabric is opaque.

An adhesive applied area 50a and an adhesive non-applied area 50b are formed on a surface of the sealing member 50, the surface facing the container main body 40. A thermoplastic adhesive (hot melt) is applied on the adhesive applied area 50a. The adhesive applied area 50a abuts on the elongated protrusion 45 provided on the flange 43 of the container main body 40. Then, an abutting portion of the sealing member 50 and the elongated protrusion 45 is warmed by a mold, so that the adhesive is melted, and the sealing member 50 and the elongated protrusion 45 are heat-fused (glued).

The adhesive is not applied on the adhesive non-applied area 50b. The adhesive non-applied area 50b is set to an area facing the filling opening 15 side of the syringes 10 held in the syringe holding member 30 (see FIG. 2).

[Syringe]

Next, the syringe 10 will be described with reference to FIG. 5.

Figure 5:
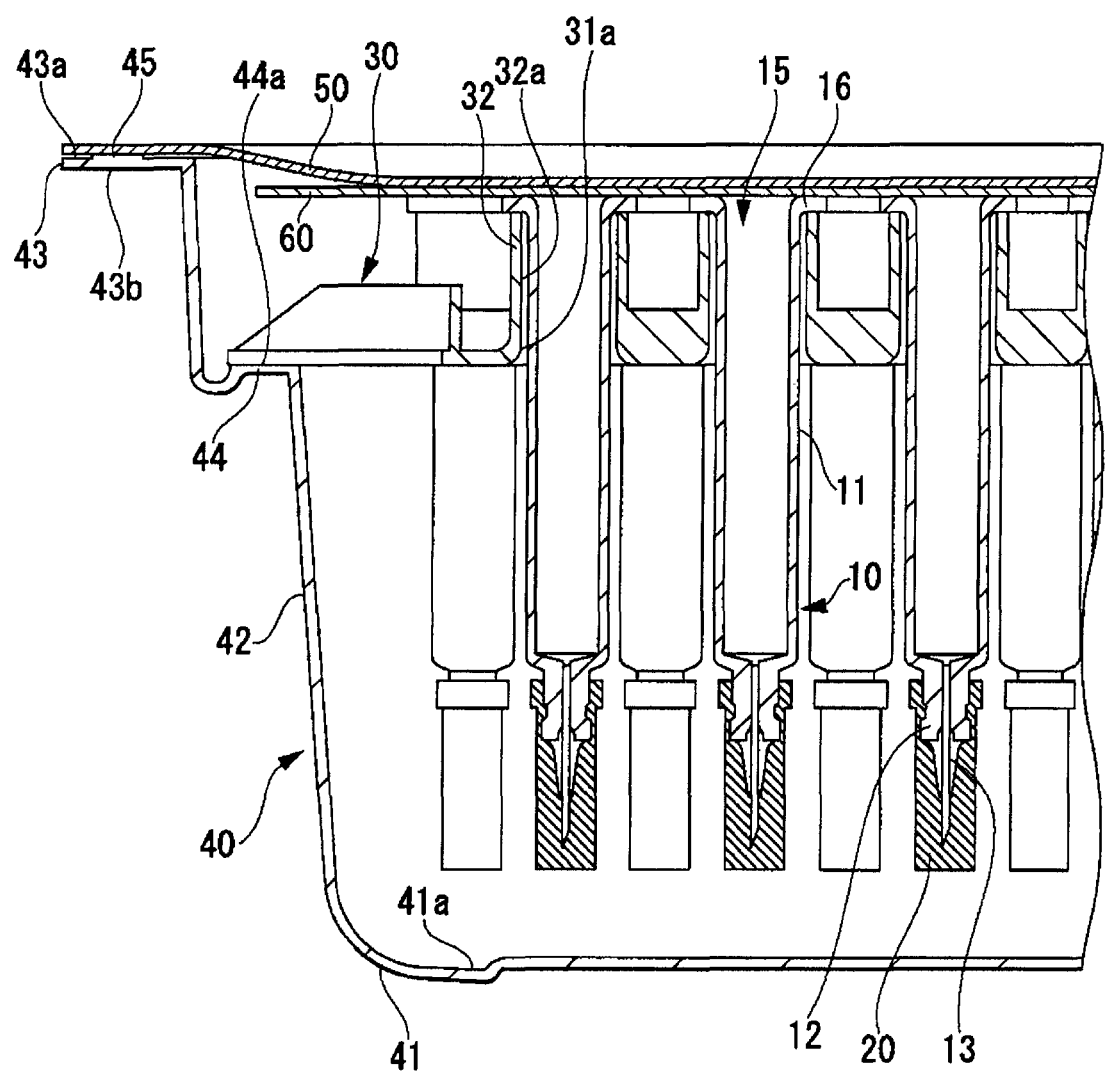
FIG. 5 is a partial longitudinal sectional view of the medical device package according to the first embodiment of the present invention.

FIG. 5 is a partial longitudinal sectional view of the syringe package 80.

As illustrated in FIG. 5, the syringe 10 includes a syringe main body 11 made of a hollow cylindrical body, a discharge portion 12 formed at a tip end side of the syringe main body 11, and a needle tube 13 fixed to the discharge portion 12. That is, the syringe storage container 1 of the present embodiment stores the syringe 10 with a needle.

An outer diameter of the syringe body is smaller than the through-hole 31a and the cylindrical hole 32a of the syringe holding member 30. A liquid chamber that accumulates a filled drug solution is formed inside the syringe main body 11. Further, the filling opening 15 for filling the drug solution into the liquid chamber of the syringe main body 11 is formed at a base end side of the syringe main body 11, the base end being opposite to the discharge portion 12.

In the present embodiment, an end surface at the filling opening 15 side of the syringe main body 11 is one end surface, and an end surface of the discharge portion 12 is the other end surface.

The flange portion 16 is provided around the filling opening 15 of the syringe main body 11, an outline of an outer periphery of the flange portion 16 being formed into an ellipse shape. At least a part (for example, a long diameter) of the outer diameter of the flange portion 16 is formed larger than the diameter of the cylindrical hole 32a of the syringe holding member 30. Therefore, the flange portion 16 of the syringe 10 that is inserted into the cylindrical hole 32a and the through-hole 31a is placed on an upper end portion of the cylinder portion 32.

Note that the shape of the flange portion 16 is not limited to the ellipse shape of the present embodiment, and may be an annulus ring shape, for example.

A cap member 20 is attached to the discharge portion 12. The member 20 is formed into an approximately cylindrical shape, and one end in an axial direction is opened, and the other end in the axial direction is closed. The cap member 20 covers the discharge portion 12 and the needle tube 13 protruding from the discharge portion 12. Examples of a material for the cap member 20 include elastic members, such as rubber and elastomer, for example.

The syringe 10 is inserted into the through-hole 31a provided in the syringe holding member 30 in a state where the cap member 20 is attached to the discharge portion 12, and is held in the syringe holding member 30.

[Method of Assembling Medical Device Package]

Next, a method of assembling the syringe package 80 will be described.

To assembly the syringe package 80, first, the syringe holding member 30 and the container main body 40 are prepared. Then, the base plate 31 of the syringe holding member 30 is placed on the mounting shelf 44 of the container main body 40. Accordingly, the syringe holding member 30 is engaged with the container main body 40.

Next, the syringe 10 is inserted into the cylindrical hole 32a and the through-hole 31a of the syringe holding member 30. The cap member 20 is attached to the discharge portion 12 of the syringe 10, in advance. Accordingly, the syringe 10 to which the cap member 20 is attached is held in the syringe holding member 30, and is stored in the container main body 40 (in the state illustrated in FIG. 3).

Next, the inner sheet 60 is placed on the flange portions 16 of a plurality of syringes 10 held in the syringe holding member 30. Accordingly, the filling opening 15 (flange portion 16) side of the plurality of syringes 10 held in the syringe holding member 30 is covered with the inner sheet 60.

Next, the sealing member 50 is placed on the elongated protrusion 45 provided on the flange 43 of the container main body 40. Then, the receiving jig (not illustrated) abuts on the lower surface 43b of the flange 43, and a warmed metal mold (not illustrated) presses the sealing member 50. Accordingly, the adhesive applied on the sealing member 50 is melted, and the sealing member 50 and the elongated protrusion 45 are heat-fused (glued), and the syringe package 80 is assembled.

Since the lower surface 43b of the flange 43 is formed into a smooth plane, the thickness of a portion of the flange 43, where the elongated protrusion 45 is provided, is secured. Accordingly, the elongated protrusion 45 is not deformed by applied heat, and the sealing member 50 and the elongated protrusion 45 are reliably heat-fused (sealed) at the time of heat fusion of the sealing member 50 and the elongated protrusion 45.

The metal mold (not illustrated) is formed into a square flat plate shape, for example, and presses the entire surface of the sealing member 50. At this time, only the elongated protrusion 45 comes in contact with the sealing member 50, and thus the sealing member 50 is not heat-fused (is not glued) to an area other than the elongated protrusion 45 of the flange 43. That is, the sealing member 50 can be always heat-fused to the elongated protrusion 45.

Further, the area of the adhesive applied area 50*a* (see FIG. 4) formed on the sealing member 50 is larger than that of the flange 43 of the container main body 40. Therefore, even if the sealing member 50 is shifted from the container main body 40 to some extent, the adhesive applied area 50*a* of the sealing member 50 can abut on the elongated protrusion 45 on the flange 43 of the container main body 40. As a result, even if the sealing member 50 is shifted from the container main body 40 to some extent, the sealing member 50 and the elongated protrusion 45 can be glued.

Further, the outline of the outer periphery of the elongated protrusion 45 provided on the flange 43 of the container main body 40 is smaller than the outlines of the outer peripheries of the flange 43 and the sealing member 50, and thus the flange 43 and an outer edge portion of the sealing member 50 are not heat-fused (sealed). Therefore, the sealing member 50 can be easily held and the peeling work of the sealing member 50 can be simply performed when the sealing member 50 is peeled from the container main body 40.

After the syringe package 80 is assembled, the syringe package 80 is packaged with a sterilization packaging bag having an opening, and the opening of the packaging bag is sealed. Next, sterilization processing using a high-temperature vapor or gas, such as high-pressure vapor sterilization (autoclave) or ethylene oxide gas (EOG) sterilization, is performed with respect to the syringe package 80 in the packed syringe packaging.

A part of the sterilization packaging bag is formed of, similarly to the sealing member 50, a material that is permeable by the gas for sterilization and is not permeable by minute particles such as bacteria or viruses. Therefore, the high-temperature vapor or gas, which is the gas for sterilization, can permeate the packaging bag and the syringe package 80. As a result, the sterilization processing can be performed with respect to an outer surface of the syringe package 80, the syringe holding member 30 in the syringe package 80, and the syringes 10 held in the syringe holding member 30.

When the sterilization processing is applied to the syringe package 80, the sealing member 50 is pressed by the high-temperature vapor or gas, and the sealing member 50 is deformed to be dented toward an inside of the container main body 40. Accordingly, the surface of the sealing member 50, the surface facing the container main body 40, abuts on the filling opening 15 side of the plurality of syringes 10 held by the syringe holding member 30 across the inner sheet 60 (see FIG. 5).

As described above, the area facing the filling opening 15 side of the plurality of syringes 10, on the surface of the sealing member 50, the surface facing the container main body 40, is the adhesive non-applied area 50*b* on which an adhesive is not applied. That is, when the high-pressure vapor sterilization is performed, the adhesive non-applied area 50*b* of the sealing member 50 is deformed toward the filling opening 15 side of the syringes, and comes in contact with the filling openings 15 through the inner sheet 60. Therefore, an area of the sealing member 50 coming in contact with the inner sheet 60 is not applied the adhesive, and thus the adhesive is not attached to the inner sheet 60. As a result, at the time of opening the syringe package 80, the inner sheet 60 is not removed together with the sealing member 50, and a state in which the filling opening 15 side of the plurality of syringes 10 is covered with the inner sheet 60 can be maintained.

Note that an area at an inner side of the flange 43, of an area (adhesive applied area 50*a*) at an outer side of a portion facing the filling openings 15 of the plurality of syringes 10, on the surface of the sealing member 50, the surface facing the container main body 40, is close to the elongated protrusion 45 that is a glued portion of the container main body 40 with the sealing member 50. Therefore, in the vicinity of the elongated protrusion 45 (glued portion), the sealing member 50 is less likely to be deformed into a direction of being closer to the filling openings 15 of the syringes 10. Therefore, the adhesive applied area 50*a* of the sealing member 50 is less likely to be in contact with the inner sheet 6Q. Further, there are no syringes 10 below the sealing member 50 in the vicinity of the elongated protrusion 45 (glued portion). Therefore, even if the sealing member 50 in the vicinity of the elongated protrusion 45 (glued portion) is deformed and comes in contact with the inner sheet 60, the inner sheet 60 is deformed along with the sealing member 50, and the adhesive is not attached enough to the inner sheet 60 to be glued with the sealing member 50.

2. Second Embodiment of Medical Device Package

[Configuration of Medical Device Package]

Next, a configuration of a medical device package according to a second embodiment will be described with reference to FIG. 6.

Figure 6:
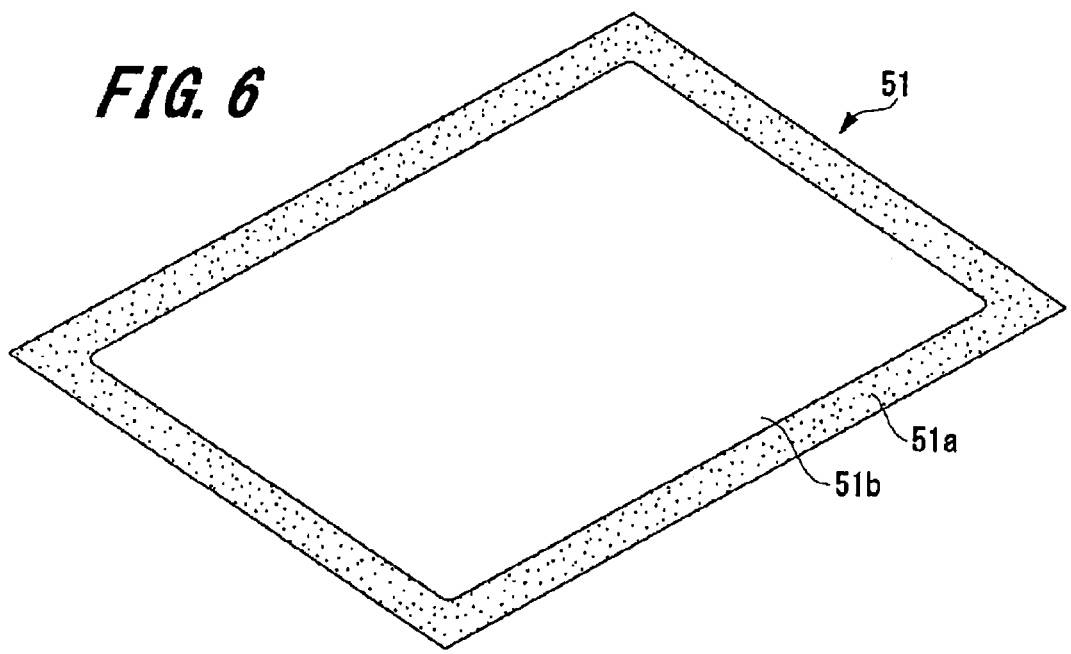
FIG. 6 is a perspective view of a sealing member in a medical device package according to a second embodiment of the present invention.

FIG. 6 is a perspective view of a sealing member in a medical device package according to the second embodiment.

The medical device package according to the second embodiment is provided with a configuration similar to the syringe package 80 (see FIG. 2) of the first embodiment. A difference of the syringe package of the second embodiment form the syringe package 80 is only a sealing member. Therefore, a sealing member 51 in the medical device package of the second embodiment will be described.

[Sealing Member]

The sealing member 51 illustrated in FIG. 6 is formed into a square sheet shape approximately equal to an outline of an outer periphery of a flange 43 (see FIG. 2) in a container main body 40. The sealing member 51 is heat-fused to the flange 43 of the container main body 40 using an adhesive. To be specific, the sealing member 51 is heat-fused to an elongated protrusion 45 of the flange 43. Differences of the sealing member 51 from the sealing member 50 (see FIG. 4) according to the first embodiment are an adhesive applied area 51*a* and an adhesive non-applied area 51*b*.

A thermoplastic adhesive (hot melt) is applied on the adhesive applied area 51*a*. The area of the adhesive applied area 51*a* is smaller than the area of the adhesive applied area 50*a* (see FIG. 4) of the sealing member 50 according to the first embodiment, but is larger than the area of the flange 43 (see FIG. 2) of the container main body 40. The adhesive applied area 51*a* abuts on the elongated protrusion 45 provided on the flange 43 of the container main body 40. Following that, the abutting portion of the sealing member 51 and the elongated protrusion 45 is warmed by a mold, so that an adhesive is melted, and the sealing member 51 and the elongated protrusion 45 are heat-fused (glued).

Further, the adhesive is not applied on the adhesive non-applied area 51*b*. The adhesive non-applied area 51*b* is set to an area facing an inner sheet 60 (see FIG. 2).

A medical device package of the second embodiment having such a configuration can also exert an effect similar to the syringe package (medical device package) 80 of the first embodiment.

For example, the area of the adhesive applied area 51*a* formed on the sealing member 51 is larger than the area of the flange 43 of the container main body 40. Therefore, even if the sealing member 51 is shifted from the container main body 40 to some extent, the adhesive applied area 51*a* of the sealing member 51 can abut on the elongated protrusion 45 on the flange 43 of the container main body 40, and the adhesive applied area 51*a* and the elongated protrusion 45 can be glued.

Further, when sterilization processing is applied to the medical device package of the second embodiment, the adhesive is not applied on an area of the sealing member 51, the area being in contact with the inner sheet 60, and thus the adhesive is not attached to the inner sheet 60. As a result, the inner sheet 60 is not removed together with the sealing member 51 at the time of opening the medical device package of the second embodiment, and a state in which a filling opening 15 side of a plurality of syringes 10 is covered with the inner sheet 60 can be maintained.

3. Third Embodiment of Medical Device Package

[Configuration of Medical Device Package]

Next, a configuration of a medical device package according to a third embodiment will be described with reference to FIG. 7.

Figure 7:
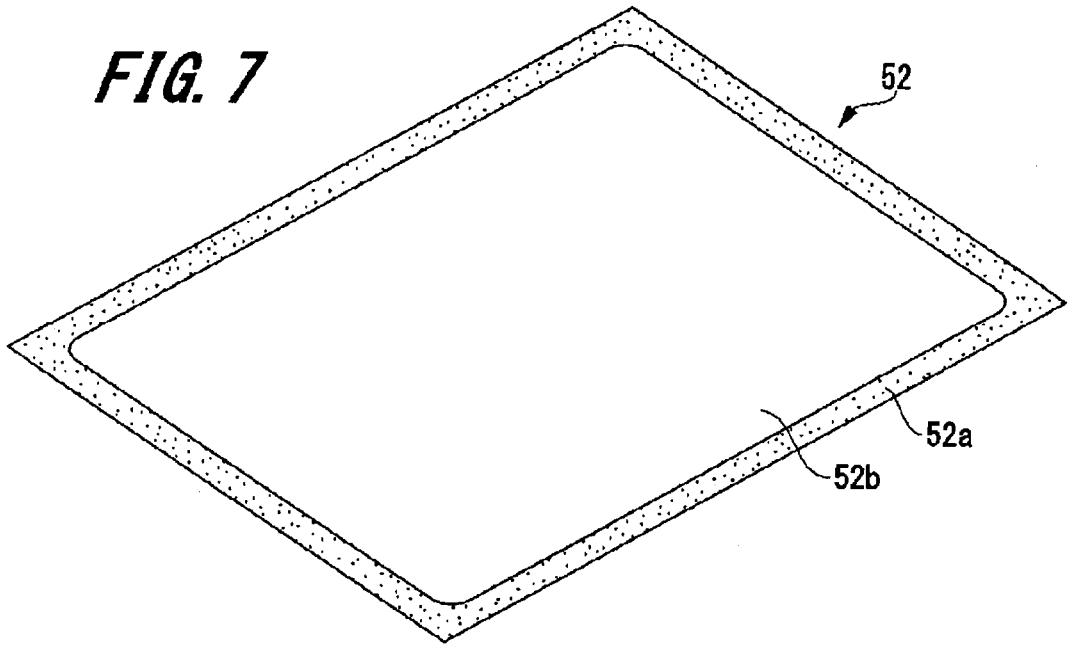
FIG. 7 is a perspective view of a sealing member in a medical device package according to a third embodiment of the present invention.

FIG. 7 is a perspective view of a sealing member in a medical device package according to the third embodiment.

The medical device package according to the third embodiment has a configuration similar to the syringe package 80 (see FIG. 2) of the first embodiment. A difference of the medical device package of the third embodiment from the syringe package 80 is only a sealing member. Therefore, here, a sealing member 52 in the medical device package of the third embodiment will be described.

[Sealing Member]

The sealing member 52 illustrated in FIG. 7 is formed into a square sheet shape approximately equal to an outline of an outer periphery of a flange 43 (see FIG. 2) in a container main body 40. The sealing member 52 is heat-fused to the flange 43 of the container main body 40 using an adhesive. To be specific, the sealing member 52 is heat-fused to an elongated protrusion 45 of the flange 43. Differences of the sealing member 52 from the sealing member 50 (see FIG. 4) according to the first embodiment are an adhesive applied area 52*a* and an adhesive non-applied area 52*b*.

A thermoplastic adhesive (hot melt) is applied on the adhesive applied area 52*a*. The area of the adhesive applied area 52*a* is smaller than the area of the adhesive applied area 50*a* (see FIG. 4) of the sealing member 50 according to the first embodiment, and is set to be approximately equal to the area of the flange 43 (see FIG. 2) of the container main body 40. The adhesive applied area 52*a* abuts on the elongated protrusion 45 provided on the flange 43 of the container main body 40. Following that, the abutting portion of the sealing member 52 and the elongated protrusion 45 is warmed by a mold, so that the adhesive is melted, and the sealing member 52 and the elongated protrusion 45 are heat-fused (glued).

The adhesive is not applied on the adhesive non-applied area 52*b*. The adhesive non-applied area 52*b* is set to an area facing an opening 40*a* (see FIG. 2).

Even the medical device package of the third embodiment having such a configuration can obtain an effect similar to the syringe package 80 (medical device package) of the first embodiment.

For example, the area of the adhesive applied area 52*a* formed on the sealing member 52 is set approximately equal to the area of the flange 43 of the container main body 40. Therefore, even if the sealing member 52 is shifted from the container main body 40 to some extent, the adhesive applied area 52*a* of the sealing member 52 can abut on the elongated protrusion 45 on the flange 43 of the container main body 40, and the adhesive applied area 52*a* and the elongated protrusion 45 can be glued.

Further, when sterilization processing is applied to the medical device package of the third embodiment, the adhesive is not applied on an area of the sealing member 52, the area being in contact with an inner sheet 60, and thus the adhesive is not attached to the inner sheet 60. As a result, the inner sheet 60 is not removed together with the sealing member 52 at the time of opening the medical device package of the third embodiment, and a state in which a filling opening 15 side of a plurality of syringes 10 is covered with the inner sheet 60 can be maintained.

4. Fourth Embodiment of Medical Device Package

[Configuration of Medical Device Package]

Next, a configuration of a medical device package according to a fourth embodiment will be described with reference to FIGS. 8 and 9.

Figure 8:
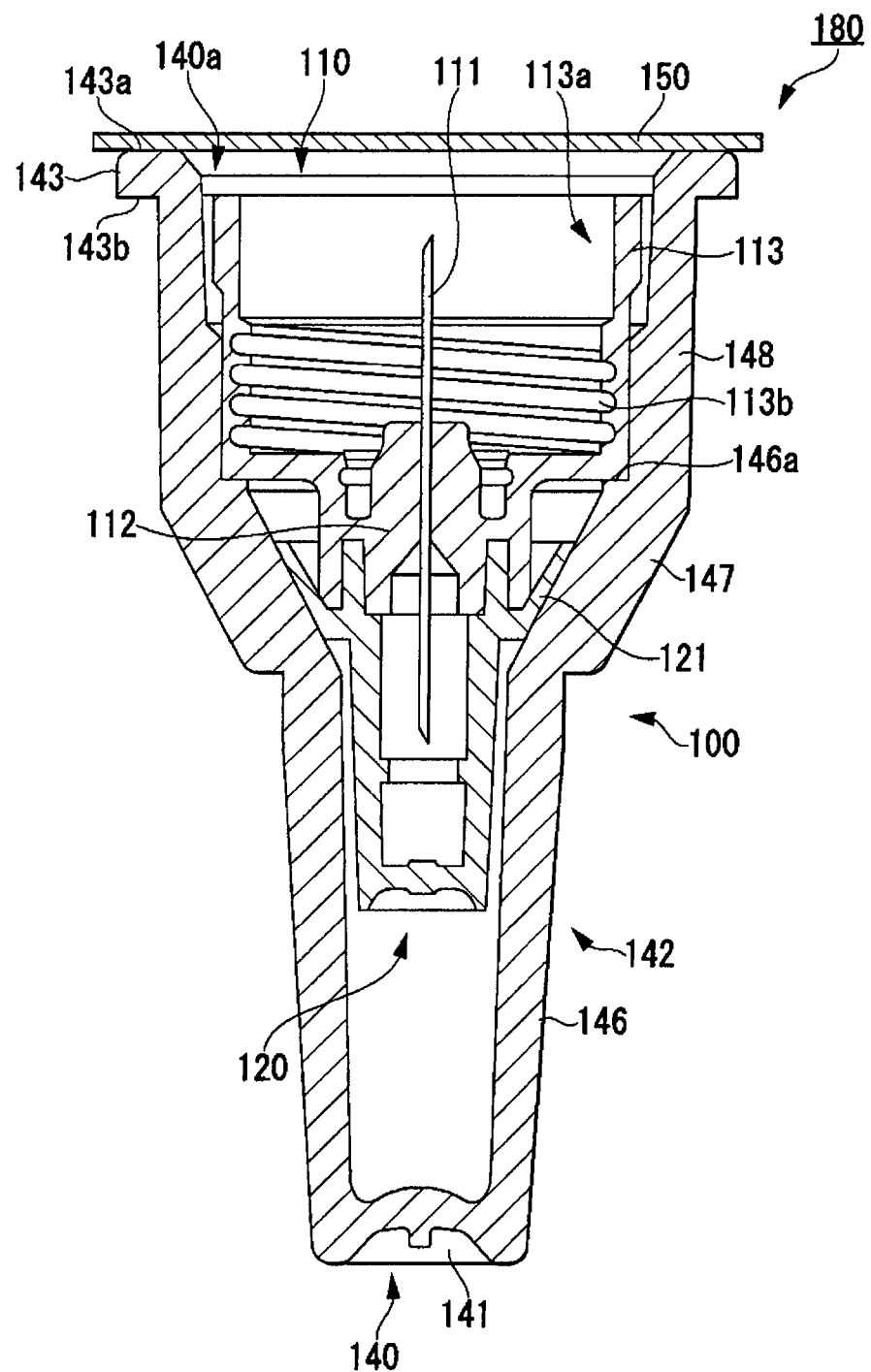
FIG. 8 is a longitudinal sectional view of a medical device package according to a fourth embodiment of the present invention.

FIG. 8 is a longitudinal sectional view of a medical device package according to the fourth embodiment of the present invention. FIG. 9 is an exploded view of the medical device package according to the fourth embodiment of the present invention.

As illustrated in FIGS. 8 and 9, a needle member package 180 representing the medical device package according to the fourth embodiment is configured from a needle member storage container 100 representing another specific example of the medical device storage container, and a needle member 110 representing another specific example of the medical device stored in the needle member storage container 100.

The needle member storage container 100 is used when the needle member 110 is conveyed/kept. The needle member storage container 100 includes a container main body 140 that holds and stores the needle member 110 and a sealing member 150.

[Container Main Body]

Next, the container main body 140 will be described.

As illustrated in FIG. 8, the container main body 140 includes a peripheral wall portion 142 including an upper end portion and a lower end portion, a bottom 141 continuing to the lower end portion of the peripheral wall portion 142 and surrounded by the lower end portion, an opening 140*a* surrounded by the upper end portion of the peripheral wall portion 142, and a flange 143 continuing to the upper end portion of the peripheral wall portion 142. An internal space of the container main body 140 surrounded by the peripheral wall portion 142, the bottom 141, and the opening 140*a* is a storage space that stores the needle member 110.

The bottom 141 is formed into an approximately circular plate shape, and configures a lower end of the container main body 140. The peripheral wall portion 142 is formed into an approximately cylindrical shape, and includes a lower cylinder 146 continuing to the bottom 141, a tapered cylinder 147 continuing to the lower cylinder 146, and an upper cylinder 148 continuing to the tapered cylinder 147. The diameter of the lower cylinder 146 is set smaller than that of the upper cylinder.

The tapered cylinder 147 is continuously increased in the diameter toward the upper cylinder 148 side. An inner surface of the tapered cylinder 147 is engaged with a cap member 120 described below attached to the needle member 110. Further, a step portion 146*a* is formed on an inner surface of the tapered cylinder 147 at the upper cylinder 148 side. A connection portion 113 described below of the needle member 110 abuts on the step portion 146a, so that the needle member 110 is held in the container main body 140. That is, the step portion 146a represents another specific example of the holding unit according to the present invention. Note that the step portion 146a may be omitted. In this case, the cap member 120 is engaged with the inner surface of the tapered cylinder 147, so that the needle member 110 is held in the container main body 140. That is, the inner surface of the tapered cylinder 147 represents another specific example of the holding unit according to the present invention.

The flange 143 is approximately perpendicular to an upper end of the peripheral wall portion 142, and is formed into an approximately circular frame shape. The flange 143 includes an upper surface 143a facing an upper end and a lower surface 143b facing a lower end. The upper surface 143a and the lower surface 143b are formed into planes.

The container main body 140 is favorably not denatured by sterilization processing using a high-temperature vapor or gas, such as high-pressure vapor sterilization (autoclave) or ethylene oxide gas (EOG) sterilization. Examples of a material for the container main body 140 include resins having excellent durability, such as polypropylene, polystyrene, polyethylene, polycarbonate, an ABS resin, and PET.

[Sealing Member]

Next, the sealing member 150 will be described.

As illustrated in FIG. 9, the sealing member 150 is formed into a sheet shape, and includes a circular portion 150a and a holding portion 150b continuing to a part of the circular portion 150a. An outer diameter of the circular portion 150a is set to be slightly larger than an outline of an outer periphery of the flange 143 of the container main body 140. The circular portion 150a of the sealing member 150 is heat-fused to the flange 143 of the container main body 140 using an adhesive. The holding portion 150b is formed into an approximately a triangle shape in which one side continues to the circular portion 150a. The holding portion 150b is not glued to the container main body 140.

It is favorable that the sealing member 150 is permeable by a gas for sterilization and is not permeable by minute particles such as bacteria or viruses. An example of a material for the sealing member 150 includes Tyvek (registered trademark) that is a high-density polyethylene nonwoven fabric manufactured by Du Pont Kabushiki Kaisha. Note that the sealing member 150 formed of the high-density polyethylene nonwoven fabric is opaque.

An adhesive applied area 151a and an adhesive non-applied area 151b are formed on a surface of the sealing member 150, the surface facing the container main body 140. A thermoplastic adhesive (hot melt) is applied on the adhesive applied area 151a. The adhesive applied area 151a abuts on the flange 143 of the container main body 140. Then, an abutting portion of the sealing member 150 and the flange 143 is warmed by a mold, so that the adhesive is melted, and the sealing member 150 and the flange 143 are heat-fused (glued).

Further, the adhesive is not applied on the adhesive non-applied area 151b. The adhesive non-applied area 151b is set to an area facing a connection portion (one end surface) 113 described below of the needle member 110 stored in the container main body 140.

[Needle Member]

Next, the needle member 110 will be described.

The needle member 110 illustrated in FIGS. 8 and 9 is attached to a syringe (a pen-type syringe, or the like), a tip portion of which is sealed with a rubber plug. The needle member 110 includes a double ended needle 111 including needles at both ends, a needle holding portion 112 that holds a middle portion of the double ended needle 111, and the connection portion 113 continuing to the needle holding portion 112.

As illustrated in FIG. 8, the needle holding portion 112 is formed into an approximately columnar shape, and holds a middle portion of the double ended needle 111. The connection portion 113 is provided continuing to a one end portion of the needle holding portion 112 in an axial direction, and is formed into an approximately cylindrical shape including a cylinder hole 113a. One end portion of the double ended needle 111 is arranged in the connection portion 113.

In the present embodiment, an end surface of the connection portion 113 at a side opposite to the needle holding portion 112 is one end surface of the needle member 110, and an end surface of the needle holding portion 112 at a side Opposite to the connection portion 113 is the other end surface of the needle member 110. The one end surface of the needle member 110 faces the sealing member 150. Further, an end surface of the connection portion 113 at a side of the needle holding portion 112 abuts on the step portion 146a of the container main body 140.

A female screw portion 113b is formed on an inner peripheral surface of the connection portion 113. A tip portion of a syringe, a tip of which is sealed with a rubber plug, is screwed with the connection portion 113. That is, a male screw portion to be screwed with the female screw portion 113b of the needle member 110 is provided at the tip portion of the syringe. When the tip portion of the syringe is connected to the connection portion 113 of the needle member 110, a needle tip formed on the one end portion of the double ended needle 111 punctures the rubber plug that seals the tip portion of the syringe. As a result, the double ended needle 111 and the internal space of the syringe communicate with each other.

The cap member 120 is attached to the needle holding portion 112. The cap member 120 is formed into an approximately cylindrical shape, and one end in the axial direction is opened and the other end in the axial direction is closed. The cap member 120 covers the other end portion of the double ended needle 111 protruding from the needle holding portion 112. Further, a protrusion 121 engaged with the inner surface of the tapered cylinder 147 in the container main body 140 is provided on an outer peripheral surface of the cap member 120.

The needle member package 180 having such a configuration can obtain an effect similar to the syringe packages of the first to third embodiments. That is, when sterilization processing is applied to the needle member package 180, the sealing member 150 is pressed to be dented toward an inner side of the container main body 140 by the high-temperature vapor or gas. Therefore, a surface of the sealing member 150, the surface facing the container main body 140, abuts on an end surface of the connection portion 113 in the needle member 110.

As described above, an area facing the connection portion 113 side, on the surface of the sealing member 150, the surface facing the container main body 140, is the adhesive non-applied area 151b where the adhesive is not applied. Therefore, if the surface of the sealing member 150, the surface facing the container main body 140, abuts on the end surface of the connection portion 113 in the needle member 110, the adhesive is not attached to the connection portion 113.

5. Modification

Embodiments of medical device packages have been described including its effect. However, the medical device packages of the present invention are not limited to the embodiments described above and illustrated in the drawings, and various modifications can be made without departing from the gist of the invention described in the claims.

For example, the medical device packages of the first to third embodiments have configurations that store the syringe 10 as a specific example of the medical device. Further, the medical device package of the fourth embodiment has a configuration that stores the needle member 110 as another specific example of the medical device. However, as the medical device according to the present invention, a connector that connects tubes, a syringe and a tube, or an agent container and a tube may be applied.

Further, in the first to fourth embodiment, the sealing members are manufactured such that the adhesive is applied on the portion serving as the adhesive applied area of a nonwoven fabric. However, a sealing member according to the present invention may be manufactured such that a nonwoven fabric formed into a size of the adhesive non-applied area is bonded to a nonwoven fabric, the entire of which is applied the adhesive.

Further, to maintain a state in which a filling opening 15 side of a plurality of syringes 10 is covered with an inner sheet 60, two sheets or more inner sheets 60 may be layered and placed on flange portions 16 of the syringes 10.

In this case, even if the adhesive is applied to the entire surface of the sealing member, the surface facing a container main body 40, a top inner sheet 60 or a several number of the inner sheets 60 from the top inner sheet 60 is glued to the sealing member. Then, the filling opening 15 side of the plurality of syringes 10 can be covered with a bottom inner sheet 60 or a several number of the inner sheets 60 from the bottom inner sheet 60.

Further, the first to third embodiments have configurations in which the medical device package includes the inner sheet 60. However, the medical device package of the present invention may have a configuration without including an inner sheet 60. For example, when a syringe package is opened in an environment without bacteria and dust and a drug solution is filled in the syringe, the bacteria and dust do not enter the syringes even if a filling opening side of the syringes is exposed. In this case, the inner sheet 60 can be omitted.

Further, in the first embodiment, the adhesive non-applied area 50b of the sealing member 50 is an area facing the plurality of syringes 10. In the second embodiment, the adhesive non-applied area 51b of the sealing member 51 is an area facing the inner sheet 60. In the third embodiment, the adhesive non-applied area 52b of the sealing member 52 is an area facing the opening 40a. However, the adhesive non-applied area according to the present invention is not limited to these embodiments, and may be an area including an area facing at least a plurality of syringes 10 and not to hinder gluing of the sealing member and the container main body.

As the adhesive non-applied area according to the present invention, an area facing a portion at an inner side of the outline of the inner periphery of the elongated protrusion 45 provided on the flange 43 of the container main body 40 may be set to the adhesive non-applied area. That is, the adhesive applied area may be set to an area facing the elongated protrusion 45. In this case, the amount of the adhesive to be used can be decreased, and thus cost required for manufacturing the medical device package can be decreased. Note that, in this case, it is necessary to highly accurately position the sealing member and the container main body to avoid gluing failure.

Further, the first to third embodiments have the configurations in which the elongated protrusion 45 that serves as the glued portion with the sealing member is provided on the flange 43 of the container main body 40. However, as the container main body according to the present invention, a container main body in which an elongated protrusion 45 is not formed on a flange 43 may be employed. In this case, the sealing member is heat-fused (is glued) to an upper surface 43a of the flange 43.

When such a container main body is used, a sealing member 50 including an adhesive applied area 50a having a larger area than the flange 43 or a sealing member 51 including an adhesive applied area 51a having a larger area than the flange 43 may be favorably employed. Accordingly, even if the sealing member 50 or 51 is shifted from the container main body to some extent, the adhesive applied area 50a or 51a abuts on the flange 43 of the container main body, and the adhesive applied area 50a or 52a and the flange 43 can be glued.

Further, in the first to third embodiments, the mounting shelf 44 is formed such that the longitudinal sectional view of the peripheral wall portion 42 is formed into a crank shape. However, as the mounting shelf according to the present invention, a protrusion portion continuing to an inner surface of a peripheral wall portion and protruding approximately parallel to a bottom 41 may be employed.

Further, the mounting shelf according to the present invention is not necessarily continuing along an inner wall surface of the peripheral wall portion in a peripheral direction, and may be provided discontinuing along the inner wall surface of the peripheral wall portion as long as the mounting shelf can support the syringe holding member. In this case, the mounting shelf may be formed of a plurality of ribs continuing to the inner surface of the peripheral wall portion and the bottom 41, and protruding approximately parallel to the bottom 41.

Further, in the first to third embodiments, the container main body 40 is formed into a box shape with an upper portion open. However, the container main body according to the present invention may be formed into a cylindrical shape with a bottom.

Further, in the first to third embodiments, description has been made taking the syringe storage container 1 and the syringe package 80 that store the syringe 10 with a needle, as examples. However, the medical device package of the present invention may store a syringe to which no needle is attached.

Further, the syringe holding member 30 of the first to third embodiment holds the syringe 10 such that the filling opening 15 faces upward (faces an upper end). However, as the method of filling a drug solution (agent) to a syringe, there is a method of filling a drug solution (agent) from a discharge portion of the syringe using a filling nozzle. When the drug solution (agent) is filled to the syringe using such a method, the syringe is held by the syringe holding member such that the discharge portion faces upward (faces an upper end). In this case, the discharge portion of the syringe also serves as a filling opening for filling the drug solution, and the discharge portion side of the syringe is the one end surface of the medical device according to the present invention.

Further, in the first to third embodiments, the sealing members formed into a square shape approximately equal to the outline of the outer periphery of the flange 43 are used. However, as the sealing member according to the present invention, a sealing member formed into a long belt shape, and wound and kept in a roll manner may be used.

A method of assembling a syringe package (medical device package) in this case is as follows. A large number of container main bodies 40 in which the syringe holding member 30 that holds the syringes 10 is mounted are arranged. Next, the sealing member enough to cover the large number of arranged container main bodies 40 is pulled out from the roll, and is placed on the elongated protrusions 45 of the large number of container main bodies 40. Following that, the sealing member is heated and pressurized by a metal mold corresponding to the size of the pulled sealing member, and the elongated protrusions 45 and the sealing member are heat-fused using an adhesive. Following that, the sealing member is cut along the outline of the outer periphery of the flange 43 in each container main bodies 40, whereby the syringe package 80 can be assembled.

Embodiments of the present invention can be used for a medical device container that stores medical devices.

What is claimed is:

1. A medical device package comprising:
    a medical device including a first end surface and a second end surface; and
    a medical device storage container storing the medical device, the medical device storage container comprising:
        a container main body including a peripheral wall portion having an upper end portion and a lower end portion, a bottom that is continuous with the lower end portion and surrounded by the lower end portion, an opening surrounded by the upper end portion, and a storage space formed inside the peripheral wall portion and the bottom, and
        a holding unit located in the storage space, and holding the medical device such that the first end surface faces upward; and
        a sealing member comprising a nonwoven fabric sheet that is permeable to gas and/or vapor but impermeable to minute particles, the nonwoven fabric sheet having a lower surface that faces the container main body,
    wherein the sealing member is glued to the container main body via a heat-melted adhesive to seal the opening of the container main body,
    wherein the lower surface of the nonwoven fabric sheet includes an adhesive applied area on which the adhesive is applied and an adhesive non-applied area on which the adhesive is not applied, the nonwoven fabric sheet being configured such that the adhesive non-applied area faces at least the first end surface of the medical device held by the holding unit,
    wherein the adhesive non-applied area is formed without bonding another sheet on the nonwoven fabric sheet, and
    wherein the sealing member is deformed such that a central portion of the sealing member protrudes toward the bottom of the container main body and such that the adhesive non-applied area of the nonwoven fabric sheet contacts the first end surface of the medical device but does not contact any portion of the bottom of the container main body.

2. The medical device package according to claim 1, wherein:
    the medical device is a syringe that includes a filling opening configured to allow a drug solution to be filled in the first end surface, and
    the holding unit comprises a syringe holding member that is engaged with an inner surface of the peripheral wall portion and adapted to hold the syringe such that the first end surface of the syringe faces upward.

3. The medical device package according to claim 2, further comprising an inner sheet adapted to cover a side of the first end surface of the syringe held by the syringe holding member,
    wherein the adhesive non-applied area of the nonwoven fabric sheet contacts the first end surface of the syringe via the inner sheet.

4. The medical device package according to claim 3, wherein the adhesive non-applied area includes at least an area facing the inner sheet.

5. The medical device package according to claim 2, wherein the syringe includes a discharge portion forming the second end surface and configured to discharge the drug solution.

6. The medical device package according to claim 1, wherein the adhesive non-applied area includes at least an area facing the opening.

7. The medical device package according to claim 1, wherein:
    the container main body includes a flange portion that is continuous with the upper end portion and surrounds the upper end portion, and
    the sealing member is glued to the flange portion.

8. The medical device package according to claim 7, wherein the central portion of the sealing member is located lower than a portion of the sealing member adjacent to the flange.

9. The medical device package according to claim 1, wherein:
    the sealing member is permeable by a high-pressure vapor, and
    the medical device stored in the container main body is a medical device that has been sterilized via a high-pressure vapor that permeates the sealing member.

10. A method of manufacturing a medical device package,
    providing a medical device including a first end surface and a second end surface; and
    providing a medical device storage container comprising:
        a container main body including a peripheral wall portion having an upper end portion and a lower end portion, a bottom that is continuous with the lower end portion and surrounded by the lower end portion, an opening surrounded by the upper end portion, and a storage space formed inside the peripheral wall portion and the bottom, and
        a holding unit located in the storage space; and
        a sealing member comprising a nonwoven fabric sheet that is permeable to gas and/or vapor but impermeable to minute particles, the nonwoven fabric sheet having a lower surface that faces the container main body;
    placing the medical device in the holding unit of the storage container such that the first end surface faces upward;
    gluing the sealing member is to the container main body via a heat-melted adhesive to seal the opening of the container main body, such that the lower surface of the nonwoven fabric sheet includes an adhesive applied area on which the adhesive is applied and an adhesive non-applied area on which the adhesive is not applied, and such that the adhesive non-applied area faces at least the first end surface of the medical device held by the holding unit, wherein the adhesive non-applied area is formed without bonding another sheet on the nonwoven fabric sheet; and sterilizing the package assembly by a high-temperature vapor or gas, so as to deform the sealing member with the high-temperature vapor or gas such that a central portion of the sealing member protrudes toward the bottom of the container main body and such that the adhesive non-applied area of the nonwoven fabric sheet contacts the first end surface of the medical device but does not contact any portion of the bottom of the container main body.

11. A medical device package comprising:

a medical device including a first end surface and a second end surface; and a medical device storage container storing the medical device, the medical device storage container comprising:

a container main body including a peripheral wall portion having an upper end portion and a lower end portion, a bottom that is continuous with the lower end portion and surrounded by the lower end portion, an opening surrounded by the upper end portion, and a storage space formed inside the peripheral wall portion and the bottom, and a holding unit located in the storage space, and holding the medical device such that the first end surface faces upward; and a nonwoven fabric sheet being permeable to gas and/or vapor but impermeable to minute particles, and having a lower surface that faces the container main body, wherein the nonwoven fabric sheet is glued to the container main body via a heat-melted adhesive to seal the opening of the container main body, wherein the lower surface of the nonwoven fabric sheet includes an adhesive applied area on which the adhesive is applied and an adhesive non-applied area on which the adhesive is not applied, the nonwoven fabric sheet being configured such that the adhesive non-applied area faces at least the first end surface of the medical device held by the holding unit, wherein the adhesive non-applied area is formed without bonding another sheet on the nonwoven fabric sheet, wherein the nonwoven fabric sheet is deformed such that a central portion of the nonwoven fabric sheet protrudes toward the bottom of the container main body and such that the adhesive non-applied area of the nonwoven fabric sheet contacts the first end surface of the medical device but does not contact any portion of the bottom of the container main body.

12. The medical device package according to claim 11, wherein the medical device storage container does not include an inner sheet under the non-woven fabric sheet.

* * * * *